United States Patent [19]

Ellenbogen

[11] 4,431,634

[45] Feb. 14, 1984

[54] PRENATAL IRON SUPPLEMENTS

[75] Inventor: Leon Ellenbogen, New City, N.Y.

[73] Assignee: American Cyanamid Company, Stamford, Conn.

[21] Appl. No.: 332,413

[22] Filed: Dec. 21, 1981

[51] Int. Cl.³ ............... A61K 33/26; A61K 31/295; A61K 33/10; A61K 33/08
[52] U.S. Cl. .................................. 424/147; 424/156; 424/157; 424/295
[58] Field of Search ............... 424/147, 156, 157, 295

[56] References Cited

U.S. PATENT DOCUMENTS

| | | | |
|---|---|---|---|
| 2,816,854 | 12/1957 | Gross | 424/147 |
| 2,823,167 | 2/1958 | Newmark | 424/295 |
| 4,171,379 | 10/1979 | Harmon et al. | 424/147 |
| 4,228,159 | 10/1980 | MacMillan | 424/147 |

Primary Examiner—Douglas W. Robinson
Attorney, Agent, or Firm—Robert P. Raymond

[57] ABSTRACT

Multimineral dietary supplement compositions of enhanced iron bioavailability are provided by the use of controlled quantities of oxides and carbonates of calcium and magnesium.

12 Claims, 4 Drawing Figures

PRENATAL IRON SUPPLEMENTS

BACKGROUND OF THE INVENTION

Mineral and vitamin compositions are commonly taken as dietary aids either as therapeutic preparations directed to a specific medical problem or as general nutritional supplements.

Iron deficiency anemias have been conventionally treated with a wide variety of compounds including elementary iron, ferrous compounds, ferric compounds and iron complexes. One of the most common forms of iron-deficiency anemia is that associated with pregnancy.

In treating iron-deficiency anemia, it is important that the bioavailability of the iron be maximized for a given iron content. Simply increasing the iron content in a unit dosage in an effort to achieve the required levels of iron absorption can cause constipation and other undesired G.I. side effects without achieving the anticipated level of absorption due to interference in the iron's absorption from other components contained in the dietary supplement composition.

SUMMARY OF THE INVENTION

This invention relates to multimineral, dietary supplement compositions for the treatment of iron deficiency anemia which provide enhanced levels of iron bioavailability. This is achieved by the use of controlled levels of oxides and carbonates of co-administered minerals, such as calcium and magnesium. The compositions are especially useful in prenatal therapy.

DETAILED DESCRIPTION OF THE INVENTION

Figure 1:
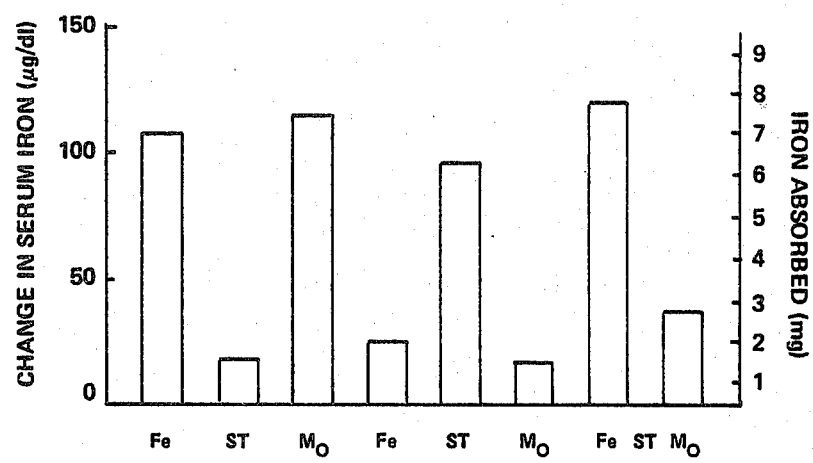

Elemental iron and a wide variety of iron compounds have been conventionally used as hematinics in the therapeutic treatment of anemias and as nutritional supplements to insure satisfaction of the bodies minimum daily recommended allowance of iron. Commonly, such agents are administered in combinations of a variety of minerals and/or vitamins for which minimum recommended daily allowances have been established.

One of the most common causes of iron-deficiency anemia is that associated with pregnancy. During pregnancy and lactation, it is common to supplement the body's enhanced need of iron, calcium, magnesium and other minerals as well as its enhanced requirements of vitamins via a prenatal multivitamin, multimineral dietary supplement.

It has now been found that the bioavailability of an iron supplement can be enhanced by controlling the levels of the oxides and carbonates of minerals such as calcium and magnesium used in the mineral supplement compositions.

Iron-deficiency anemias can be treated by oral administration of soluble iron salts in the ferrous or ferric state, e.g., ferrous chloride, ferrous fumarate, ferrous gluconate and ferric ammonium citrate as well as in the form of natural and synthetic complexes of iron and elemental iron.

Recommended minimum daily requirements of iron and a variety of other minerals such as calcium, potassium, magnesium, copper and zinc have long been established together with minimum daily requirements of a variety of vitamins such as A, D, E, C, $B_1$, $B_2$, $B_6$ and $B_{12}$. Such minerals and vitamins are commonly prescribed in combination as a daily dietary supplement as well as for the therapeutic treatment of specific medical problems associated with specific deficiencies.

It has now been found that the combined quantities of oxides and carbonates of the minerals coadministered with the iron play a substantial role in the bioavailability of the iron component and that the control of the upper limit of the combined quantities enhances the absorption of the iron supplement. Calcium and magnesium present principle problems in that magnesium is commonly employed in the form of magnesium oxide and calcium is commonly employed in the form of calcium carbonate.

While calcium and magnesium are almost always present in multi-mineral compositions, especially in the case of prenatal compositions, they are less necessary from a dietary supplement point of view in that adequate quantities of each can be maintained through proper diet. In contrast, however, prenatal supplementation of iron is very important.

Accordingly, in the compositions of the present invention, the quantities of calcium and magnesium can be reduced to zero. The coadministered minerals such as calcium and magnesium when present in their oxide and carbonate form should not exceed 300 mg and 75 mg per unit dosage respectively. These quantities and those appearing below are based upon the elemental metal rather than the oxide or carbonate salts or other salts used unless otherwise indicated. More preferred compositions contain calcium carbonate with calcium at the 250 mg level or less per unit dosage and magnesium oxide with the magnesium present at the 25 mg level or less per unit dosage.

It is preferred to administer the compositions of the present invention in the form of tablets; however, any conventional form of orally administering vitamins can be used. Conventionally used iron compounds and formulation methods as well as pharmaceutically acceptable formulation aids and adjuvants are well known in the patent and technical literature, e.g., U.S. Pat. No. 2,823,167 to H. L. Newmark; U.S. Pat. No. 2,816,854 to R. H. Gross and Remington's Practice of Pharmacy, Martin and Cook (1961) see page 46 et seq. for hematopoietics.

It will also be understood that the invention is not limited to the materials, proportions, methods and the like specifically described and exemplified below, which can be modified without departing from the scope of the invention.

EXAMPLE 1

A film coated tablet for use as a prenatal multi-vitamin-mineral supplement with enhanced iron bioavailability was prepared with each tablet containing about the International Units (I.U.) or mg. of ingredients listed below. The percentage of U.S. Recommended Daily Allowance of the components for pregnant or lactating women is listed in parentheses thereafter. The conventional formula which it replaces is set forth for purposes of comparison:

|  | New Formulation MB | Conventional Formulation MO |
|---|---|---|
| Vitamin A Acetate | 8,000 I.U. | 8,000 I.U. |
| Vitamin D | 400 I.U. | 400 I.U. |
| Vitamin E | 30 I.U. | 30 I.U. |

|  | New Formulation MB | Conventional Formulation MO |
|---|---|---|
| (as dl-Alpha Tocopheryl Acetate) | | |
| Vitamin C | 100 mg | 120 mg |
| (Ascorbic Acid) | | |
| Folic Acid | 1 mg | 1 mg |
| Thiamine | 3 mg | 3 mg |
| (as Thiamine Mononitrate Vitamin $B_1$) | | |
| Riboflavin | 3.4 mg | 3.4 mg |
| (Vitamin $B_2$) | | |
| Vitamin $B_6$ | 4 mg | 4 mg |
| (as Pyridoxine Hydrochloride) | | |
| Niacinamide | 20 mg | 20 mg |
| Vitamin $B_{12}$ | 12 mcg | 12 mcg |
| (Cyanocobalamin) | | |
| Calcium | 250 mg | 350 mg |
| (as Calcium Carbonate) | | |
| Iodine | 0.3 mg | 0.3 mg |
| (as Potassium Iodide) | | |
| Elemental Iron | 60 mg | [60 mg] |
| (as Ferrous Fumarate) | | |
| Magnesium | 25 mg | [100 mg] |
| (as Magnesium Oxide) | | |
| Copper | 2 mg | 2 mg |
| (as Cupric Oxide) | | |
| Zinc | 25 mg | 15 mg |
| (as Zinc Sulfate) | | |
| Docusate Sodium USP (DSS) | 50 mg | 50 mg |

The absorption of iron was established by collection of venous blood samples collected by hypodermic syringe and clotted at room temperature for one hour in silicone coated glass tubes. The tubes were centrifuged at 4,000 g for 30 minutes at 4° C. to isolate the serum which is removed and stored at −20° C. The serum samples were assayed for serum iron via spectrophotometry using ferrozine reagent.

In addition to testing the above formulations for iron absorption, various other commercial formulations designated as ST, MO, NL and NF are included for comparative purposes, together with a slurry of ferrous fumarate per se and ferrous fumarate taken with various combinations of calcium carbonate, calcium sulfate, magnesium oxide and magnesium hydroxide. The "New Formulation" above is referred to as MB. A formulation identical to MB except with regard to the calcium carbonate level was prepared and labeled MA. Formulation MA contains 350 mg of calcium carbonate. The Conventional Formulation is referred to as MO below.

The tests were conducted in healthy menstruating female volunteers 21 to 45 years of age having normal hemoglobin and hematocrit valves. The subjects fasted overnight. Fifteen to 24 subjects were used in each study. Each study was conducted as a randomized crossover trial with the composition being administered at 8 a.m. at 3 to 4 day intervals. Blood was first taken in the fasting state. Then the preparation was administered using 50 ml of deionized water and the subjects remained fasting until the final blood sample was obtained. Serum iron levels were assayed in duplicate on a blind basis.

Changes in serum iron concentration were measured in 24 subjects after ingestion of 50 ml of deionized water alone showed a mean increase in serum iron concentration of 2.3 ug per 100 ml per hour. All valves were corrected using this valve for diurnal variation. Values for iron absorption were calculated from the increases in serum iron concentration measured 2 to 6 hours after iron ingestion.

As a control, serum iron concentration was also measured after oral administration of 65 mg of elemental iron given in the form of a ferrous fumarate slurry. A valve of 8.0 mg for mean iron absorption was calculated for the iron administered alone. Since the mean valves for the change in serum iron concentration were very similar at 2, 4 and 6 hours after ingestion, all subsequent studies of iron absorption were performed using only fasting and 3 hour post ingestion serum iron concentrations.

The results of these studies are shown in Table I below. In each case, the quantities of mineral stated are on the basis of the elemental metal as opposed to the weight of the entire salt.

TABLE I

SUMMARY OF IRON FORMULATIONS AND IRON ABSORPTION IN VARIOUS EXPERIMENTS

| Iron Preparation | Amount of iron Ingested (mg) | Form and amount of calcium and magnesium present or (added) at the time of ingestion | | | | Calculated mean values for iron absorption in various studies | | | | |
|---|---|---|---|---|---|---|---|---|---|---|
| | | Calcium sulfate (mg) | Calcium carbonate (mg) | Magnesium oxide (mg) | Magnesium hydroxide (mg) | Study I (mg) | Study II (mg) | Study III (mg) | Study IV (mg) | Average (mg) |
| Ferrous fumarate | 65 | — | — | — | — | 8.0 | 9.0 | — | 7.3 | 8.1 |
| ST | 65 | 200 | — | 100 | — | 2.0 | — | 1.3 | 2.2 | 1.8 |
| MO | 60 | — | 350 | 100 | — | 2.8 | — | — | — | |
| Ferrous fumarate | 65 | (200) | — | — | — | — | 9.5 | — | — | |
| Ferrous fumarate | 65 | — | (350) | — | — | — | 6.8 | — | — | |
| Ferrous fumarate | 65 | — | — | (100) | — | — | 6.6 | — | — | |
| Ferrous fumarate | 65 | (200) | — | (100) | — | — | 6.2 | — | — | |
| Ferrous fumarate | 65 | — | (350) | (100) | — | — | 4.3 | — | — | |
| New Formulation A | 60 | — | 350 | 25 | — | — | — | 3.0 | — | |
| New Formulation B | 60 | — | 250 | 25 | — | — | — | 5.0 | 4.1 | 4.5 |
| NL | 60 | — | 200 | — | 100 | — | — | — | 2.4 | |
| NF | 65 | — | 350 | 100 | — | — | — | — | 3.0 | |

The results reported in Table I above are graphically depicted in FIGS. 1-4. In each case, the bar graphs show the mean values of the points observed.

FIG. 1 shows the results of Study I using ferrous fumarate alone (Fe) and commercial product ST and conventional formulation MO with serum iron concentrations measured at 2, 4 and 6 hours after ingestion. This study involved 15 female subjects of child bearing age.

Figure 2:
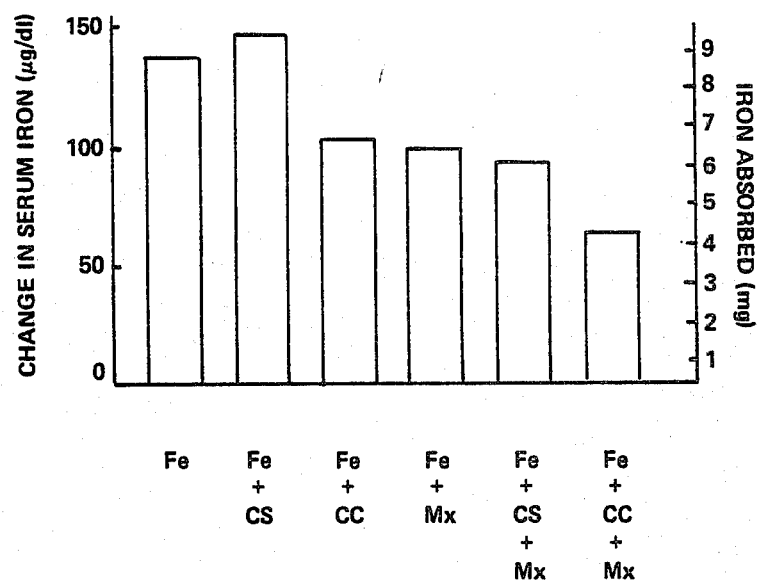

FIG. 2 shows the results of Study II establishing the effects on iron absorption of calcium sulfate, calcium carbonate, magnesium oxide and combination of these calcium and magnesium salts. The additive inhibitory effects on iron absorption due to calcium carbonate and magnesium oxide can be seen therefrom. Plaster of paris does not seem to be inhibitory perhaps due to the formation of an inert state. Again, 15 females of child bearing age were studied using ferrous fumarate alone and in combinations of calcium sulfate (CS), calcium carbonate (CC) and magnesium oxide (MX). The study involved 15 females of child bearing age with data obtained three hours after oral ingestion.

Figure 3:
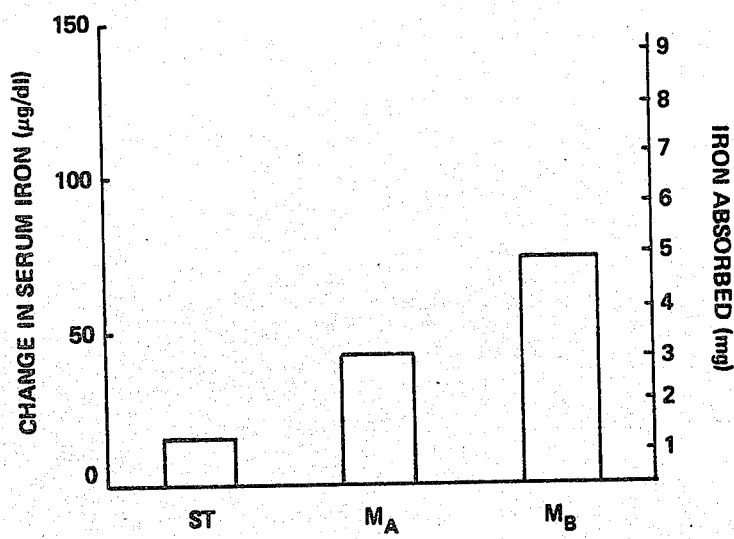

FIG. 3 shows the changes in serum iron concentration in 15 females of child bearing age from Study III using commercial products ST and new formulations MA and MB. The data were obtained 3 hours after oral ingestion.

In new formulation MA the level of calcium carbonate was maintained at 350 mg of elemental calcium and the level of elemental magnesium in the form of magnesium oxide was reduced from 100 mg to 25 mg. In new formulation MB the level of calcium in the form of calcium carbonate was reduced to 250 mg and the amount of elemental magnesium in the form of magnesium oxide was reduced to 25 mg.

The level of mean iron absorption in new formulation MA was increased to 3.0 mg from 1.3 mg in the commercial ST product. In new formulation MB the level was increased to 5.0 mg, dramatically showing the depressant effects of the calcium carbonate and magnesium oxide mineral components on the bioavailability of the iron supplement.

Figure 4:
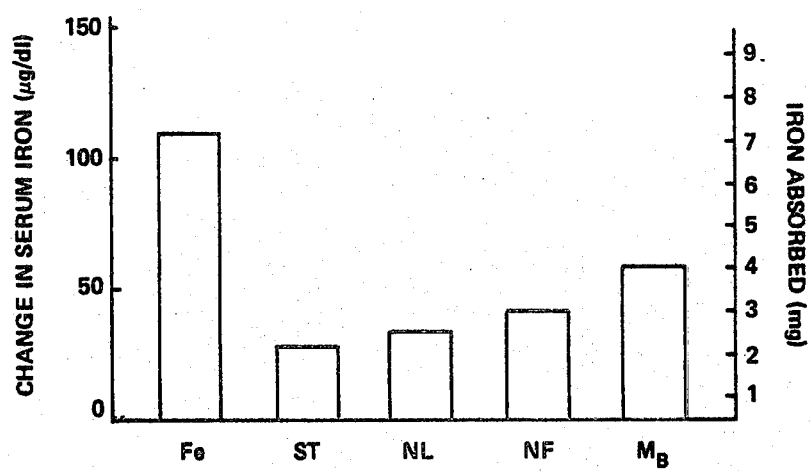

FIG. 4 shows the results from Study IV. The graph contrasts the results achieved with new formulation MB in comparison to three commercial formulations ST, NL and NF with a ferrous fumarate control (Fe).

Again, the composition of the present invention afforded an iron level of 4.1 mg versus absorption levels of 2.2 mg; 2.4 mg; and 3.0 mg of absorbed iron for the three commercial preparations respectfully.

I claim:

1. A method of enhancing the absorption of iron in multimineral, iron-supplement preparations comprising the use of limited quantities of oxides and carbonates of calcium and magnesium administered in said preparations to not more than 300 mg and 75 mg respectively per unit dosage based upon the weight of elemental calcium and magnesium in said oxide and carbonate salts.

2. A method according to claim 1 wherein the calcium is administered in the form of calcium carbonate.

3. A method according to claim 2 wherein the calcium carbonate is present in from 150 mg to 275 mg per unit dosage based on the weight of calcium in said calcium carbonate and the iron supplement is selected from the group consisting of ferrous fumarate, ferrous gluconate and ferrous sulfate.

4. A method according to claim 3 wherein the preparation contains from about 45 mg to about 65 mg of iron supplement based on elemental iron.

5. A method according to claim 1 wherein the magnesium is in the form of magnesium oxide.

6. A method according to claim 5 wherein the magnesium oxide is present in from 15 mg to 50 mg per unit dosage based on the weight of magnesium in said magnesium oxide and the iron supplement is selected from the group consisting of ferrous fumarate, ferrous gluconate and ferrous sulfate.

7. A method according to claim 6 wherein the preparation contains from about 45 to about 65 mg of iron supplement based on elemental iron.

8. A method according to claim 1 wherein said preparation is a prenatal, multivitamin, multimineral composition in solid unit dosage form containing sufficient international units of the essential vitamins and minerals to provide 100% of the minimum recommended daily allowance with the exception of calcium and magnesium which are present as calcium carbonate and magnesium oxide in amounts of not greater than about 250 mg per unit dose and about 25 mg per unit dose respectively.

9. A multimineral, iron-supplement preparation providing enhanced absorption of iron from said multimineral preparation comprising in combination with said mineral and iron supplements, oxides and carbonates of calcium and magnesium of not more than 300 mg and 75 mg respectively per unit dosage based upon the weight of elemental calcium and magnesium in said oxide and carbonate salts said preparation further characterized as containing calcium carbonate present in from 150 mg to 275 mg per unit dosage based on the calcium in said calcium carbonate and the iron supplement is selected from the group consisting of ferrous fumarate, ferrous gluconate and ferrous sulfate.

10. A composition according to claim 9 containing from about 45 mg to about 65 mg of iron supplement based on the weight of elemental iron.

11. A multimineral, iron-supplement preparation providing enhanced absorption of iron from said multimineral preparation comprising in combination with said mineral and iron supplements, oxides and carbonates of calcium and magnesium of not more than 300 mg and 75 mg respectively per unit dosage based upon the weight of elemental calcium and magnesium in said oxide and carbonate salts further characterized in that said preparation contains magnesium oxide present in from 15 mg to 50 mg per unit dosage based on the weight of magnesium in said magnesium oxide and the iron supplement is selected from the group consisting of ferrous fumarate, ferrous gluconate and ferrous sulfate.

12. A composition according to claim 11 wherein the preparation contains from about 45 to about 65 mg of iron supplement based on elemental iron in said supplement.

* * * * *